United States Patent [19]
Marx et al.

[11] 4,328,800
[45] May 11, 1982

[54] AUTOMATED INTRAVENOUS FLUID REGULATING AND ADMINISTERING APPARATUS

[75] Inventors: Alvin J. Marx, 107 Georgian Court Rd., Rochester, N.Y. 14610; Darold C. Wobschall, Williamsville, N.Y.

[73] Assignee: Alvin J. Marx, Rochester, N.Y.

[21] Appl. No.: 202,412

[22] Filed: Oct. 30, 1980

[51] Int. Cl.³ .............................................. A61M 5/00
[52] U.S. Cl. .................................................. 128/214 E
[58] Field of Search .................................... 128/214 E

[56] References Cited

U.S. PATENT DOCUMENTS

| | | | |
|---|---|---|---|
| 3,609,379 | 9/1971 | Hildebrandt | 128/214 E |
| 4,001,801 | 1/1977 | Moulet | 128/214 E |
| 4,002,996 | 1/1977 | Klebanoff et al. | 128/214 E |
| 4,111,198 | 9/1978 | Marx et al. | 128/214 E |
| 4,114,144 | 9/1978 | Hyman | 128/214 E |
| 4,173,224 | 11/1979 | Marx et al. | 128/214 E |
| 4,181,130 | 1/1980 | Bailey | 128/214 E |

*Primary Examiner*—William E. Kamm
*Attorney, Agent, or Firm*—Stephen B. Judlowe

[57] ABSTRACT

Automated dispensing apparatus is disclosed for administering intravenous fluid to a patient under gravity pressure at a controlled volumetric rate, such that deviations from a desired fluid volumetric rate are automatically corrected. In accordance with the invention the area and maximum width of each fluid drop are measured with two intersecting light beams. Apparatus, responsive to each of the light beams, generates signals representative of drop area and width, and these two parameters are combined to obtain a signal proportional to drop volume. The measured drop volume signal is compared with a rate control signal to automatically correct the fluid flow rate.

10 Claims, 6 Drawing Figures

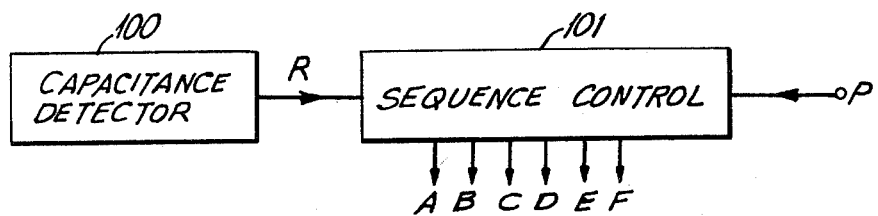
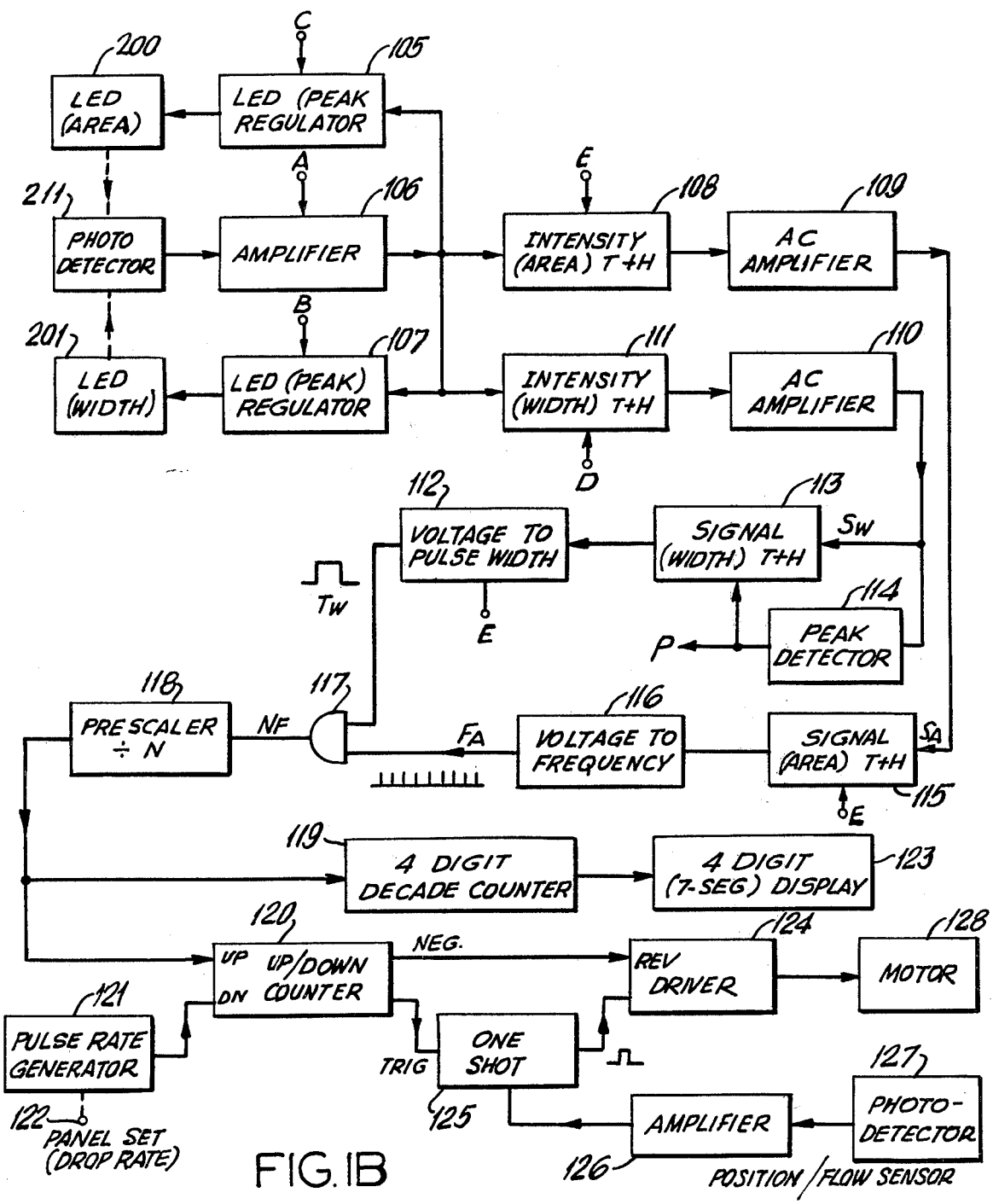
FIG. 1A
FIG. 1B

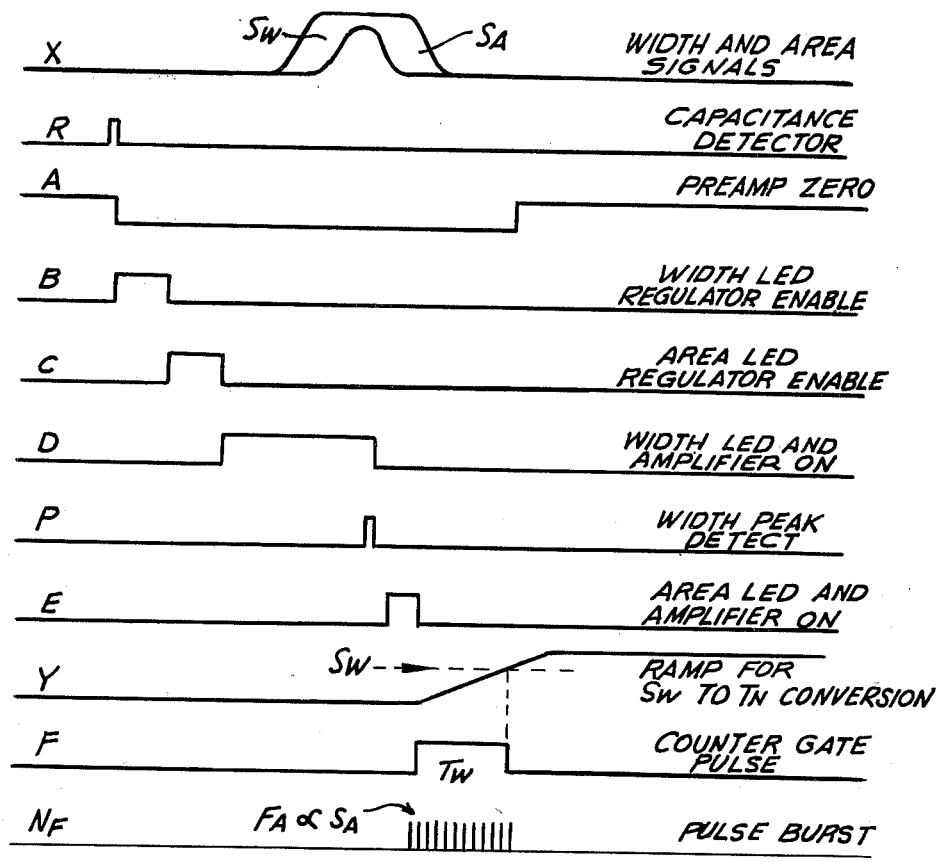
FIG. 3
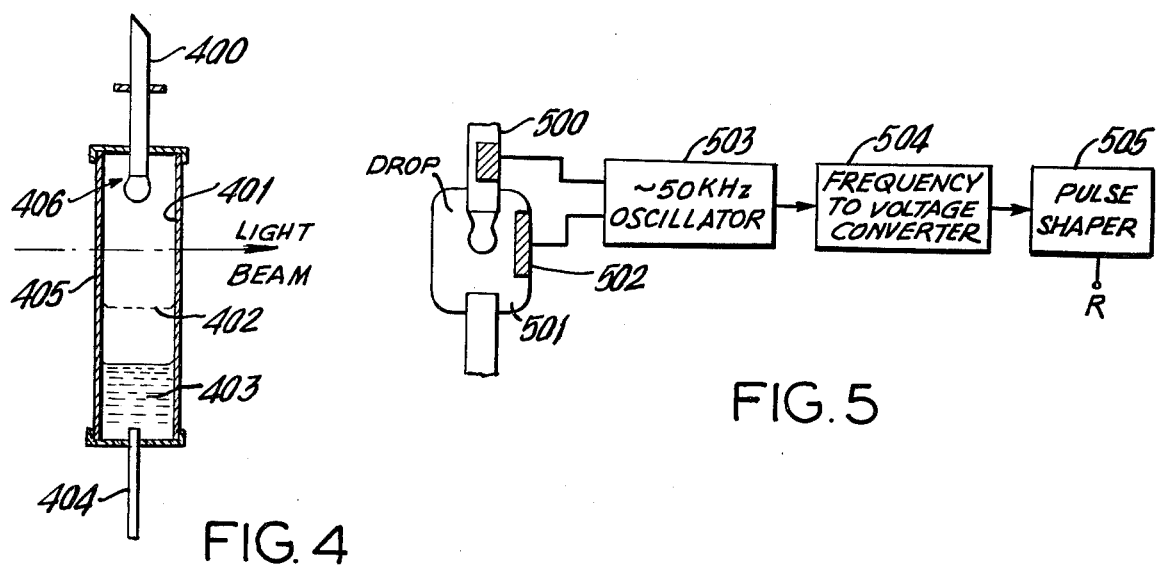
FIG. 4
FIG. 5

AUTOMATED INTRAVENOUS FLUID REGULATING AND ADMINISTERING APPARATUS

DISCLOSURE OF THE INVENTION

This invention relates to medical electronics and, more specifically, to improved intravenous flow regulation apparatus.

The intravenous administration of nutrients, electrolyte solution, and/or the like in the form of liquid drops is a common practice, particularly for postoperative patients. Such a fluid delivery system typically is comprised of a source container, a drop chamber, tubing, and an administrating needle.

The introduction of fluids intravenously is commonly specified by the physician in volumetric units, such as cc per hour. In practice, however, the actual flow rate of intravenous fluid may vary markedly from the physician's specification, primarily as a result of the patient's movements during intravenous feeding. Such patient movement is likely to retard the flow of intravenous fluid to the patient or to cease the flow of intravenous fluid altogether in the event the needle becomes obstructed. The patient's movements may also cause the intravenous fluid to flow too rapidly or at too great a rate such as when the patient changes position. In either event, the patient does not receive the proper amount of nutrient or the like and, in extreme cases, this may result in the death of the patient.

In U.S. Pat. No. 4,111,198, a system is described for automatically controlling the flow of intravenous fluid by maintaining the rate, at which drops of fluid are applied to the patient per hour at a preset level. Thus, if the fluid is being applied at too great a rate, that condition is sensed and the tube flow resistance is automatically increased, thereby decreasing the fluid flow rate. Conversely, when the fluid flow rate is sensed as being below the desired level, the fluid tube flow resistance is automatically reduced, thereby increasing the drop rate to the desired value.

This system ensures administration of intravenous fluids at the desired drop rate. However, for this system to be totally effective in achieving the desired volumetric control over the rate of fluid introduction, the fluid drops must be normalized for variation in drop volume. The drop volume changes with rate of flow, time, and type of fluid administered.

U.S. Pat. No. 4,173,224, a continuation-in-part application of U.S. Pat. No. 4,111,198, describes a system for determining the volume of each drop administered to a patient. As described in this patent the width and silhouette of each fluid drop are measured and appropriate signals generated which represent these two parameters. The signals are then multiplied to obtain a signal proportioned to the volume of the drop and this signal is combined with a rate control signal to reflect deviations in the measured drop volume from a nominal value. Deviations from the nominal rate are used to adjust the actual rate of drop administration, ensuring that fluid is supplied to the patient at the desired volumetric rate.

Although the system described in U.S. Pat. No. 4,173,224 greatly improves the intravenous administration of fluid over existing methods, it has been determined that certain techniques are helpful in further improving the accuracy of this system.

It is therefore an object of the present invention to provide an intravenous fluid administering apparatus having a high degree of accuracy in controlling the volumetric fluid administration rate.

It is a further object of the present invention to provide an accurate intravenous fluid administering apparatus which is low in cost and readily manufactured.

The above and other objects of the present invention are realized in an automated intravenous fluid administration apparatus which regulates the rate of fluid flow by the selective constriction of a fluid passing tube. A drop sensor circuit monitors the rate at which the fluid is being administered and also measures the volume of each drop.

Drop volume is measured by apparatus including at least two light sources, radiation emanating from each of said sources being directed along light paths perpendicular to each other, the light paths intersecting at a sensing point in a drop chamber through which each fluid drop passes. Associated circuitry detects the presence of a drop just prior to passing through the sensing point and also determines the maximum width of each drop. The drop chamber is advantageously constructed with clear plastic walls coated with an anti-fogging agent or alternatively the walls are heated to prevent fogging that would reduce the accuracy of the volume measurements. The measured drop volume is used to make necessary modifications to the fluid flow rate, thereby maintaining accurate and automatic control over the volumetric rate of intravenous fluid flow to the patient.

The above and other features and advantages of the present invention will become more clear from the following detailed description of a specific illustrative embodiment thereof, presented hereinbelow in conjunction with the accompanying drawings, in which:

FIGS. 1(a) and (b) are block diagrams of one embodiment of a drop volume monitor in accordance with the instant invention;

FIG. 3 is a timing diagram illustrating the operation of the circuitry in FIGS. 1(a) and 1(b);

FIG. 4 illustrates a drop chamber utilized with the apparatus in FIG. 2, and

FIG. 5 illustrates apparatus for detecting the presence of a fluid drop prior to entering the drop chamber.

Figure 2:
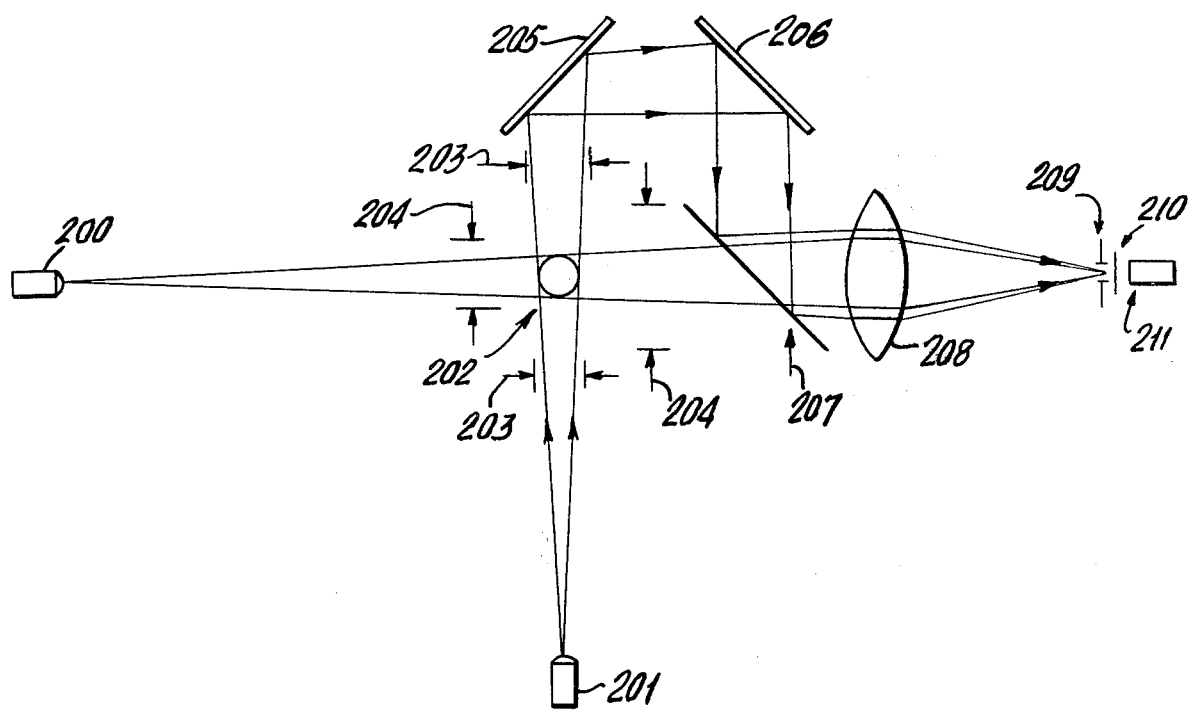
FIG. 2 illustrates an optical system for accurately determining drop volume when used in conjunction with the circuitry shown in FIGS. 1(a) and (b)

Referring now to FIGS. 1(a) and (b), there is schematically shown an automated and regulated apparatus for intravenously injecting a fluid, such as an electrolyte solution, nutrients, or the like, into a patient, the volumetric or flow rate of administration being specified by the setting of a panel control (not shown) allowing flow rates to be set in the range of 1 to 99 milliliters/minute. The rate signal developed by the panel control is applied to terminal 122 and from there to pulse rate generator 121, the operation of which will be described hereinafter.

The apparatus employs a bidirectionally operative motor 128, of the type described in U.S. Pat. No. 4,173,224, which drives a clamping mechanism (not shown), as by a worm gear, to partially pinch off fluid-delivering tubing to a proper degree such that the actual volumetric fluid flow rate to the patient is that specified by the panel control. To the extent that the actual flow rate, as measured in terms of the rate of drops per unit time, deviates from the specified rate, the apparatus, in a manner more fully discussed below, causes the motor to turn in a direction, and by an amount, to cause the proper fluid flow rate by varying the inner delivery tube cross-sectional area, and thus its flow resistance. Thus, the motor is made to move in a direction either to unconstrict the tubing, i.e., create a larger inner cross-section to increase the rate of fluid flow, if it is determined that the volumetric flow rate is less than the rate specified by the setting of the panel control, or to pinch off the tube (reduce its inner cross-sectional area) if fluid is flowing at too high a rate, that is, greater than the desired rate as established by the setting of the panel control.

FIG. 2 illustrates an optical system utilized in accordance with this invention. Light sources 201 and 200 are Light Emitting Diodes (LEDs) and are switched on alternately (as described hereinafter) to measure the width and area of a fluid drop. LED 201 is utilized for the width measurement and LED 200 is used for the area measurement. Light emanating from the light sources is selected to lie along perpendicular paths by apertures 203 and 204, and the paths intersect at sensing point 202 through which each fluid drop is passed. Light from LED 200 passes through sensing point 202, half silvered mirror 207, lens 208, aperture 209, a diffusion screen 210 and is applied to photodetector 211. Similarly light from source 201 passes through sensing point 202, is reflected from mirrors 205, 260 and 207, passes through lens 208, aperture 209 and diffusion screen 210 and is also applied to photodetector 211.

The arrangement of FIG. 2 differs from the arrangement shown in U.S. Pat. No. 4,173,224 in that two perpendicular light beams are used rather than one, and also the width (w) is measured in a plane perpendicular to the projected area plane. Analysis has shown that the use of two perpendicular light beams results in greater accuracy for volume measurements, particularly if the drop is tumbling.

In accordance with the teachings in U.S. Pat. No. 4,173,224 a drop of fluid is approximately ellipsoidal in shape. The true volume of an ellipsoid is equal to:

$$Vt = (4/3)\pi w h^2 \qquad (1)$$

where w is equal to drop width and h is equal to drop height. It has been determined that an accurate approximation of drop volume can alternatively be expressed by the relationship:

$$V = (4/3)\pi w A = C_v S_w S_A \qquad (2)$$

where w is the drop width in the X—Y plane, A is the drop area in the X—Z plane, $S_w$ is a signal voltage proportional to drop width, $S_A$ is a signal voltage proportional to drop area and $C_v$ is a calibration constant. Apparatus to determine drop volume in accordance with expression (2) and to control the fluid application rate will now be described in detail.

Referring first to FIG. 4, there is illustrated a drop chamber through which each fluid drop passes prior to administration to the patient. The drop chamber is attached, via tubing 400, to a standard bottle (not shown) containing the fluid to be administered to the patient. Fluid passes out of the drop chamber via tubing 404. A drop formation apparatus 406 permits the fluid to be dispensed into the chamber one drop at a time. The walls of the chamber at 405 are clear plastic or glass and are designed to permit the light beams emanating from the light sources discussed above to pass through the chamber with a minimum of distortion. The passage of a light beam through the chamber is schematically illustrated in FIG. 4. It is, of course, understood that the sensing point 202 referred to in FIG. 2 lies in the path of the light beams passing through the drop chamber.

To eliminate fogging of the drop chamber walls at 401, the walls are coated with a wetting agent, such as Hydron. Fogging, of course, distorts the passage of the light beams and would reduce the accuracy of the measurement system. An alternative to the anti-fogging coating on the chamber walls is an external heater (not shown), capable of heating the walls near the beam to a few degrees above ambient temperature which also eliminates fogging. Arranged beneath the light beam passage area but above the fluid level at 403 is a splash suppressor 402, preferably comprising a coarse wire mesh, designed to disperse the drop and thus reduce splashing onto the walls. In addition, the drop chamber is somewhat longer than normal to provide room for the passage of the light beam and the splash suppressor. Utilization of splash suppressor 402 prevents splash back onto the chamber walls which could also cause distortion of the light beam.

Referring now to FIGS. 1(a) and 1(b), the measurement sequence commences when a drop is released from drop apparatus 406 (FIG. 4). Before the drop passes the sensing point it is detected by capacitance detector 100 (described hereinafter), resulting in the generation of ready signal R which is applied to sequence control circuitry 101. Circuitry 101 generates a number of sequence control signals (A-F) utilized in conjunction with the circuitry in FIG. 1(b) with each signal generated being illustrated in FIG. 3. The details of sequence control circuit 101 are not given as such details are apparent to one skilled in this art by reference to the wave forms shown in FIG. 3. Circuitry necessary to generate such wave forms can be found, for example, in "Pulse Digital And Switching Wave Forms", by: Millman & Taub McGraw-Hill, 1966. The purpose of the capacitance detector is to limit the electrical energy requirements of the system by controlling the time the LEDs are on.

Referring to FIG. 3, it is seen that after ready pulse R is generated, signal A drops to a low level, a width LED enable signal B is produced and immediately thereafter an area LED enable signal C is produced. Signal A dropping to a low level enables amplifier 106, the output of which was previously clamped to zero, to eliminate stray background light effects. Signal B enables the width LED and the width LED regulator circuit 107 and signal C enables the area LED and the area LED regulator circuit 105. The function of regulator circuits 105 and 107 is to automatically adjust the current supplied to the width and area LEDs so that the base line of the photodetector 211 remains constant during the measurement process.

Subsequent to the generation of signal C width intensity amplifier 111 is turned on by pulse D. The output of LED 201 is detected by photodetector 211 and its output is in turn amplified by amplifier 106. The output of amplifier 106 is fed back to regulator 107 to maintain the width LED current at a constant level during the measurement process. The output of amplifier 106 is also applied to enabled width intensity amplifier 111, which is a track and hold amplifier designed to store a signal proportional to the width of the detected drop. The output signal from width intensity amplifier 111 is amplified by AC amplifier 110 and applied to peak detector 114. Peak detector 114 produces a pulse P when the signal generated by width intensity amplifier 111 reaches a maximum. Due to the shape of the drop this signal maximum will occur when the drop is in the center of the beam. Signal P, is used to briefly switch on width track and hold amplifier 113, causing this amplifier to store the maximum width signal for later use. Signal P is also applied to sequence control 101 and in response thereto the sequence control returns signal D to its previous state and generates signal E. Signal E is slightly delayed to permit the width track and hold amplifier 113 time to store the width signal.

Subsequent to width LED 201 and width amplifier 111 being disabled by pulse D, the area intensity amplifier 108 is enabled by pulse E. The output of the area LED is detected by photodetector 211, and its output is in turn amplified by amplifier 106 and applied to area regulator 105 to regulate the area LED current in the same manner regulator 107 regulates the width LED output. The output signal from amplifier 106 is stored in area intensity amplifier 108, and the output of amplifier 108 is in turn amplified by amplifier 109 and applied to area track and hold amplifier 115. Amplifier 115 is enabled by wave form E and stores the signal representative of drop area for use at a later time. At this time therefore signal voltages proportional to drop width ($S_w$) and drop area ($S_a$) have been obtained and stored in amplifiers 113 and 115, respectively. The signal voltages are shown at line X in FIG. 3.

To determine drop volume in accordance with expression (2); it is necessary to obtain a digital signal proportional to the product of analog signals $S_w$ and $S_a$. This is accomplished with a circuit which combines analog-to-digital conversion (single ramp method), and the product function. More particularly, voltage to frequency converter 116 produces a pulse train with a frequency $F_a$ proportional to the area signal stored in amplifier 115. A ramp signal (line Y, FIG. 3) is generated by voltage to pulse width converter 112 with the generation of the ramp being initiated by the trailing edge of timing signal E. Converter 112 produces a counter gate pulse $T_w$ when the width signal voltage, $S_w$, stored in amplifier 113 is greater than the ramp voltage. This relationship is illustrated at lines Y and F in FIG. 3. Therefore the pulse duration of signal $T_w$ is proportional to the drop width. Gate 117 allows the area frequency signal $F_a$ to pass only when enabled by pulse $T_w$. The pulses passed through gate 117 are stored in counter 218 and the number of pulses for each drop is determined by the following relationship:

$$N_f = T_w F_a = KWA$$

where K is a calibration constant.

Several gain or conversion factors would effect the calibration constant, such as the slope of the ramp generator. However once the calibration constant is set for a particular instrument it should infrequently or never require recalibration if quality components are used.

It is necessary that frequency $F_a$ be high enough to ensure that the count stored in counter 118 has the required resolution, preferably greater than 100 for 1% accuracy. Counter 118 performs a prescaling function so that the number of pulses at the output of counter 118 is numerically equal to the volume in milliliters or tenths of milliliters. The output of counter 118 is applied to four digit decade counter 119 and four digit display 123. The count is accumulated in counter 119 and display 123 records drop volume directly in milliliters.

The output of counter 118 is also applied to up/down counter 120. The up/down counter counts up in response to the output of counter 118 and counts down in response to the output of pulse rate generator 121. The output frequency of the pulse rate generator is set by a panel control (not shown) which applys a frequency control signal to terminal 122. The panel control permits the desired rate of application to be set in the range of 1 to 99 milliliters per minute. Pulse rate generator 121 generates a pulse train having a frequency proportional to the setting on the panel control.

The count stored in counter 120 determines the operation of motor 128. More particularly, if the count is close to zero motor driver 124 is disabled and motor 128 remains off. Therefore the clamping mechanism associated with the motor (described above) maintains its preset position, thereby maintaining a preset flow rate through the tube feeding the drop chamber. If the net count in countler 120 differs from zero by a predetermined amount after a certain interval, (e.g., every eight drops or equivalent period), a trigger signal is applied to one shot (monostable multivibrator) 125. The signal generated by one shot 125 is applied to motor driver 124 and will operate the motor for a period proportional to the width of the pulse generated by the one shot. If the count is positive the motor closes the clamping mechanism. If the count is negative a reverse signal is applied to motor driver 124, the motor direction is reversed, and the clamp is opened.

Pulse width of the output of the one shot is determined by photodetector 127 and amplifier 126. More particularly, an optical assembly (not shown) generates a light beam with an intensity proportional to the flow rate and the light beam is focused on photodetector 127. The output signal from photodetector 127 is therefore proportional to the clamp displacement and thus the flow rate. The photodetector output signal is applied to amplifier 126, which in turn generates a signal to control the width of the output pulse of one shot 125. In this manner therefore the period of operation for motor 128 is determined by the clamp position. The objective of this arrangement is to avoid overshoot and to obtain proper flow control over a period of seconds rather than minutes. If left on continuosly the motor operates the clamp from full open to full close in approximately 10 to 30 seconds. Added features (not shown) are to detect large counter values, increase motor speed proportionally, and to sound an alarm indicating an undesirable large deviation between desired and actual delivered volume.

Referring now to FIG. 5, there is shown the capacitive detector 100 previously described. When a drop from drop apparatus 500 passes electrodes 502 in body 501, their capacitance changes and a frequency shift occurs in the output of oscillator 503. The shift in frequency is detected by frequency to voltage converter 504 and in response thereto an AC output pulse is produced. The pulse is shaped by pulse shaper 505 and used as the ready signal described above.

The above described arrangement is merely illustrative of the principals of the present invention and numerous modifications and adaptions thereof will be readily apparent to those skilled in the art without departing from the spirit and scope of the present invention.

What is claimed is:

1. An intravenous fluid regulator apparatus comprising:
   means for generating a first signal representing a desired rate of introduction of drops of intravenous fluid to a patient,
   means for sensing the volume of each of said drops of fluid, said sensing means including at least two light sources, radiation emanating from each of said sources being selected to lie along light paths perpendicular to each other, said light paths intersecting at a sensing point through which each fluid drop passes,
   means responsive to said sensing means for generating a second signal bearing a relation to drop volume, and for operatively combining said first and second signals to produce a fluid introduction rate control signal.

2. An intravenous fluid regulator apparatus in accordance with claim 1, wherein there is further included means for detecting a fluid drop prior to the time said fluid drop passes through said sensing point and means responsive to said detecting means for enabling said sensing means.

3. An intravenous fluid regulator in accordance with claim 2, wherein there is further included means for determining the maximum width of said fluid drop as it passes through said sensing point.

4. An intravenous fluid regulator in accordance with claim 3, wherein said sensing means further includes means responsive to one of said light sources for producing a signal proportional to the area of a fluid drop, means responsive to the other of said light sources for producing a signal proportional to the maximum width of said fluid drop and means for operatively combining said proportional area signal and said proportional width signal to produce said second signal.

5. An intravenous fluid regulator in accordance with claim 4, wherein said first and second signal combining means include means for accumulating a count signal in response to said second signal, means for decreasing said accumulated count signal in response to said first signal and means for varying said fluid introduction rate control signal in response to the magnitude of said accumulated count signal.

6. An intravenous fluid regulator in accordance with claim 1, wherein said sensing point lies within a drop chamber, said drop chamber having clear plastic walls coated with an anti-fogging agent to prevent distortion of the radiation emanating from said light sources.

7. An intravenous fluid regulator in accordance with claim 1, wherein said sensing point lies within a drop chamber, said drop chamber having clear plastic walls and means for heating said clear plastic walls a predetermined number of degrees above ambient temperature.

8. An intravenous fluid regulator in accordance with claims 6 or 7, wherein said drop chamber is cylindrical in shape with a top aperture to admit said fluid drops, a bottom aperture to exit said fluid drops, and an apertured member dividing said drop chamber into upper and lower chamber portions.

9. An intravenous fluid regulator in accordance with claim 8, wherein said sensing point lies within said upper chamber and said bottom chamber contains accumulated fluid, said apertured member comprising a coarse wire mesh, whereby said fluid drops are dispersed when passing through said apertured member and splashback into said upper chamber is reduced.

10. An intravenous fluid regulator in accordance with claims 6 or 7, wherein said drop chamber has glass walls.

* * * * *